US008216555B2

(12) United States Patent
Nieuwenhuijsen

(10) Patent No.: US 8,216,555 B2
(45) Date of Patent: Jul. 10, 2012

(54) COMPOSITION OF A WATER-SOLUBLE SUNSCREEN PREPARATION FOR ACNE ROSACEA

(76) Inventor: Bart Willem Nieuwenhuijsen, Philadelphia, PA (US)

( * ) Notice: Subject to any disclaimer, the term of this patent is extended or adjusted under 35 U.S.C. 154(b) by 297 days.

(21) Appl. No.: 12/371,327

(22) Filed: Feb. 13, 2009

(65) Prior Publication Data

US 2009/0202460 A1 Aug. 13, 2009

Related U.S. Application Data

(60) Provisional application No. 61/028,285, filed on Feb. 13, 2008.

(51) Int. Cl.
*A61K 8/18* (2006.01)
*A61Q 17/04* (2006.01)

(52) U.S. Cl. ........................................... 424/60; 424/59

(58) Field of Classification Search ........................ None
See application file for complete search history.

(56) References Cited

U.S. PATENT DOCUMENTS

| | | | | |
|---|---|---|---|---|
| 4,193,989 | A * | 3/1980 | Teng et al. | 424/60 |
| 5,514,437 | A * | 5/1996 | Tanner et al. | 424/63 |
| 5,603,923 | A * | 2/1997 | Robinson et al. | 424/60 |
| 5,972,993 | A * | 10/1999 | Ptchelintsev | 514/449 |
| 7,262,158 | B1 * | 8/2007 | Lukenbach et al. | 510/122 |
| 2003/0031634 | A1 * | 2/2003 | Grune | 424/59 |
| 2004/0081681 | A1 * | 4/2004 | Vromen | 424/449 |
| 2004/0167046 | A1 * | 8/2004 | Lukenbach et al. | 510/135 |
| 2005/0196361 | A1 * | 9/2005 | Grune | 424/59 |
| 2005/0209130 | A1 * | 9/2005 | Patt | 514/6 |
| 2006/0233725 | A1 * | 10/2006 | Grune | 424/59 |
| 2007/0243271 | A1 * | 10/2007 | Hernandez et al. | 424/729 |
| 2009/0047310 | A1 | 2/2009 | Meybeck | |

OTHER PUBLICATIONS

Landers et al.; Contact urticaria, allergic contact dermatitis, and photoallergic contact dermatitis from oxybenzone; Am J Contact Dermat.; Mar. 2003; 14(1): 3304.
Nedorost, Susan T.; Facial erythema as a result of benzophenone allergy; J Am Acad Dermatol; vol. 49, No. 5; Nov. 2003; S259-S261.
Levy, Stanley B. MD; Tanning Preparations; Dermatologic—Medical Journal Clinics; Oct. 2000; 7 pages; vol. 18, Issue 4; W.B. Sanders Company; Unknown (presumed U.S.).
Petersen, Anita B. et al.; Dihydroxyacetone, the active browning ingredient in sunless tanning lotions, induces DNA damage, cell-cycle block and apoptosis in cultured HaCaT keratinocytes; Mutation Research (Genetic Toxicology and Enviromental Mutagenesis); 2004; pp. 173-186; 560 (2004); Elsevier B.V.; Unknown.
Jung, K.; UV-generated free radicals (FR) in skin; Their prevention by sunscreens and their induction by self-tanning agents; Spectrochimica Acta Part A; Copyright 2007; pp. 1423-1428; Part A 69 (2008); Elsevier B.V.; Unknown.
Unknown author(s); Dihydroxyacetone; Wikipedia; Downloaded Jan. 2012 from http://www.wikipedia.org/; Unknown date of first publication.

* cited by examiner

*Primary Examiner* — Robert A Wax
*Assistant Examiner* — Olga V Tcherkasskaya
(74) *Attorney, Agent, or Firm* — Stephen G. Stanton, Esq.

(57) ABSTRACT

The object of the invention is to provide a topical preparation for (acne) rosacea and other sensitive skin types that protects the face from harmful UV rays without the use of chemical sunscreen ingredients. It has long been found that chemical sunscreen ingredients (most popular are oxybenzone and avobenzone) can cause an increase of rosacea symptoms (flushing, erythema, papules) (Nedorost (2003) and Landers et al., 2003). Furthermore, typical waterproof sunscreen preparations also contain various forms of silicones that are used to increase the hydrophobicity of the sunscreen. These waterproof sunscreen preparations impair the release of heat from the skin. The combination of this "trapped heat" and a sensitivity to chemical sunscreen ingredients, is harmful to rosacea skin. Therefore, a sunscreen preparation that is water-soluble and uses alternative UV absorbing and UV scattering ingredients would be very useful in protecting rosacea skin from harmful UV rays.

1 Claim, No Drawings

COMPOSITION OF A WATER-SOLUBLE SUNSCREEN PREPARATION FOR ACNE ROSACEA

The present invention claims priority to U.S. provisional application 61/028,285 filed Feb. 13, 2008. This invention relates to a composition of a water-soluble sunscreen preparation for acne rosacea. The invention is comprised of Titanium Dioxide (Titanium (IV) Oxide), 5-Hydroxy-Tryptophan, Histidine, and N-AcetyL-Tyrosine.

SUMMARY

The present formulation is a topical skin care treatment that is water soluble and protects individuals with (acne) rosacea, or other sensitive skin types, from harmful UV rays without the use of chemical sunscreen ingredients that can cause an increase in skin inflammation, skin flushing and skin erythema (Nedorost (2003) and Landers et al., 2003).

DESCRIPTION

The present invention claims priority to U.S. provisional application 61/028,285 filed Feb. 13, 2008. This invention relates to a composition of a water-soluble sunscreen preparation for acne rosacea. The invention is comprised of the following components:

(1) Titanium dioxide (CAS number: 13463-67-7). The present formulation contains Titanium dioxide (Titanium (IV) oxide), chemical formula $TiO_2$, dispersed in the final gel at a concentration of about 1% to about 8%. Titanium dioxide is a white solid mineral that is not soluble in water. Titanium dioxide has a very high refractive index (n=2.7) and is used in the present formulation to reflect harmful UV rays, (2) 5-Hydroxy-Tryptophan. The present formulation contains *Griffonia simplicifolia* extract, which naturally contains 5-Hydroxy-Tryptophan. The present formulation includes *Griffonia simplicifolia* extract at a concentration of about 0.2% to about 3% (w/v, using dried extract). 5-Hydroxy-Tryptophan is a natural amino acid that absorbs UV rays. The present formulation uses *Griffonia simplicifolia* extract since it naturally contains 5-Hydroxy-Tryptophan and because *Griffonia simplicifolia* extract adds a light brown color to the final preparation, which makes it easier to blend the sunscreen preparation with the color of the skin (since Titanium dioxide is pure white), (3) Histidine (CAS number 71-00-1). Histidine is used in the present formulation at a concentration of about 0.5% to about 3%. Histidine is a natural amino acid that absorbs UV rays, and (4) N-AcetyL-Tyrosine. N-AcetyL-Tyrosine is an acetylated derivative of the essential amino acid L-Tyrosine and is used in the present formulation in place of L-Tyrosine, due to its greater solubility in water. The formulation includes N-AcetyL-Tyrosine at a concentration of about 0.5% to about 5%.

The present formulation is a topical skin care treatment that is water soluble and protects individuals with (acne) rosacea, or other sensitive skin types, from harmful UV rays without the use of chemical sunscreen ingredients that can cause an increase in skin inflammation, skin flushing and skin erythema (Nedorost (2003) and Landers et al., 2003). Such chemical sunscreen ingredients are often used in waterproof sunscreens or sunblock preparations and include: p-aminobenzoic acid (PABA), oxybenzone, dioxybenzone, avobenzone, octyl methoxycinnamate, octocrylene, octyl salicylate, sulisobenzone.

In the present formulation, Titanium dioxide (dispersed in the gel) will reflect UV rays and a blend of amino acids 5-Hydroxy-Tryptophan, Histidine and N-AcetyL-Tyrosine will absorb UV rays that have not been reflected.

The formulation is used by applying a thin layer of the sunscreen preparation to the entire face. When the application is still wet, the individual will be able to see the Titanium dioxide particles, which will enable the individual to determine if enough sunscreen is applied. Since the formulation is water-soluble (with Titanium dioxide particles dispersed throughout), it will need to be re-applied after sweating and swimming. Under dry conditions, the present formulation will provide protection from harmful UV rays for up to 2 hours, depending on the time of day and geographical location. The present formulation is a topical skin care treatment to protect the skin from harmful UV rays. The formulation is water-soluble and is gel-based, which consists of a polymer of Carbomer-940 neutralized with triethanolamine.

The formulation can be structured differently by dissolving titanium dioxide, 5-Hydroxy-Tryptophan, Histidine and N-AcetyL-Tyrosine in a different water-soluble gel base, which can be either Carbomer-based (including but not limited to: Carbomer 672, Carbomer 690, Carbomer 910, Carbomer 934, Carbomer 941, Carbomer 1342 or Carbomer 1622) or natural (including but not limited to: xanthan gum or guar gum). Additionally, the formulation can be structured differently by using Tryptophan instead of 5-Hydroxy-Tryptophan and L-Tyrosine instead of N-AcetyL-Tyrosine, although Tryptophan and L-Tyrosine are more hydrophobic than 5-Hydroxy-Tryptophan and N-AcetyL-Tyrosine. Furthermore, the present formulation can be structured differently by including the amino acid phenylalanine (although the present inventor does not include phenylalanine in the present formulation due to health risks). It can also be stated that a similar objective may be reached by including peptides containing the amino acids Tryptophan, Tyrosine, Histidine and Phenylalanine in various forms. The above-mentioned peptides can be made more water-soluble by adding polar side group to the amino acids.

The present invention may also be beneficial in protecting other sensitive skin types from UV rays. These sensitive skin types include, but are not limited to, skin disorders such as psoriasis, contact dermatitis, acne vulgaris (regular acne).

The invention claimed is:

1. A topical skin care water soluble, non-comedogenic, gel formulation to protect skin from ultraviolet rays consisting essentially of:

titanium dioxide dispersed in the gel at a concentration of about 1 to 8% w/v;

5-hydroxy-tryptophan dispersed in the gel at a concentration of about 0.2 to 3.0% w/v;

histidine in the gel at a concentration of about 0.5% to 3.0% w/v; and

N-acetyl-tyrosine dispersed in the gel at a concentration of about 0.5 to 5.0% w/v, wherein the 5-hydroxy-tryptophan is added in a form of a *Griffonia simplicifolia* extract.

* * * * *